US010791927B2

(12) United States Patent
Moreau et al.

(10) Patent No.: US 10,791,927 B2
(45) Date of Patent: Oct. 6, 2020

(54) PASSIVE SENSING MEANS FOR A PHYSIOLOGICAL PARAMETER MONITORING SYSTEM

(71) Applicant: OPHTIMALIA, Colombelles (FR)

(72) Inventors: Oliver Moreau, Cahagnes (FR); Franck Pasquette, Colombelles (FR); Xavier Razavet, Cairon (FR); Luc Mezenge, Rots (FR); Philippe Cauvet, Caen (FR); Peter Biermans, Bieville-Beuville (FR)

(73) Assignee: Ophtimalia, Colombelles (FR)

( * ) Notice: Subject to any disclaimer, the term of this patent is extended or adjusted under 35 U.S.C. 154(b) by 442 days.

(21) Appl. No.: 15/524,408

(22) PCT Filed: Nov. 2, 2015

(86) PCT No.: PCT/EP2015/075382
§ 371 (c)(1),
(2) Date: May 4, 2017

(87) PCT Pub. No.: WO2016/071252
PCT Pub. Date: May 12, 2016

(65) Prior Publication Data
US 2018/0279875 A1    Oct. 4, 2018

(30) Foreign Application Priority Data
Nov. 6, 2014    (EP) .................................... 14306781

(51) Int. Cl.
*A61B 3/16*        (2006.01)
*A61B 3/107*       (2006.01)

(52) U.S. Cl.
CPC ................ *A61B 3/16* (2013.01); *A61B 3/107* (2013.01)

(58) Field of Classification Search
None
See application file for complete search history.

(56) References Cited

U.S. PATENT DOCUMENTS

| 2002/0193674 A1 | 12/2002 | Fleischman et al. |
| 2013/0225968 A1 | 8/2013 | Auvray et al. |
| 2014/0296688 A1 | 10/2014 | Lam et al. |

FOREIGN PATENT DOCUMENTS

| CN | 103747720 | 4/2014 |
| EP | 0061777 A2 | 10/1982 |

(Continued)

OTHER PUBLICATIONS

Extended European Search Report, dated Apr. 22, 2015 in European Patent Application No. 14306781.7.

(Continued)

*Primary Examiner* — Eric F Winakur
*Assistant Examiner* — Marjan Fardanesh
(74) *Attorney, Agent, or Firm* — Barnes & Thornburg LLP; Jeffrey R. Stone

(57) ABSTRACT

The invention relates to a passive sensing means (100) for a contact lens of a physiological parameter monitoring system, for detecting variations of a physiological parameter, in particular intraocular pressure, the passive sensing means (100) forming a resonant circuit comprising an inductor (101) and at least one capacitor (121, 122, 123, 124, 125, 126). The inductor (101) and said at least one capacitor (121, 122, 123, 124, 125, 126) are coplanar in only one layer. The invention also relates to a corresponding physiological parameter monitoring system.

20 Claims, 9 Drawing Sheets

(56) References Cited

FOREIGN PATENT DOCUMENTS

Figure 1:
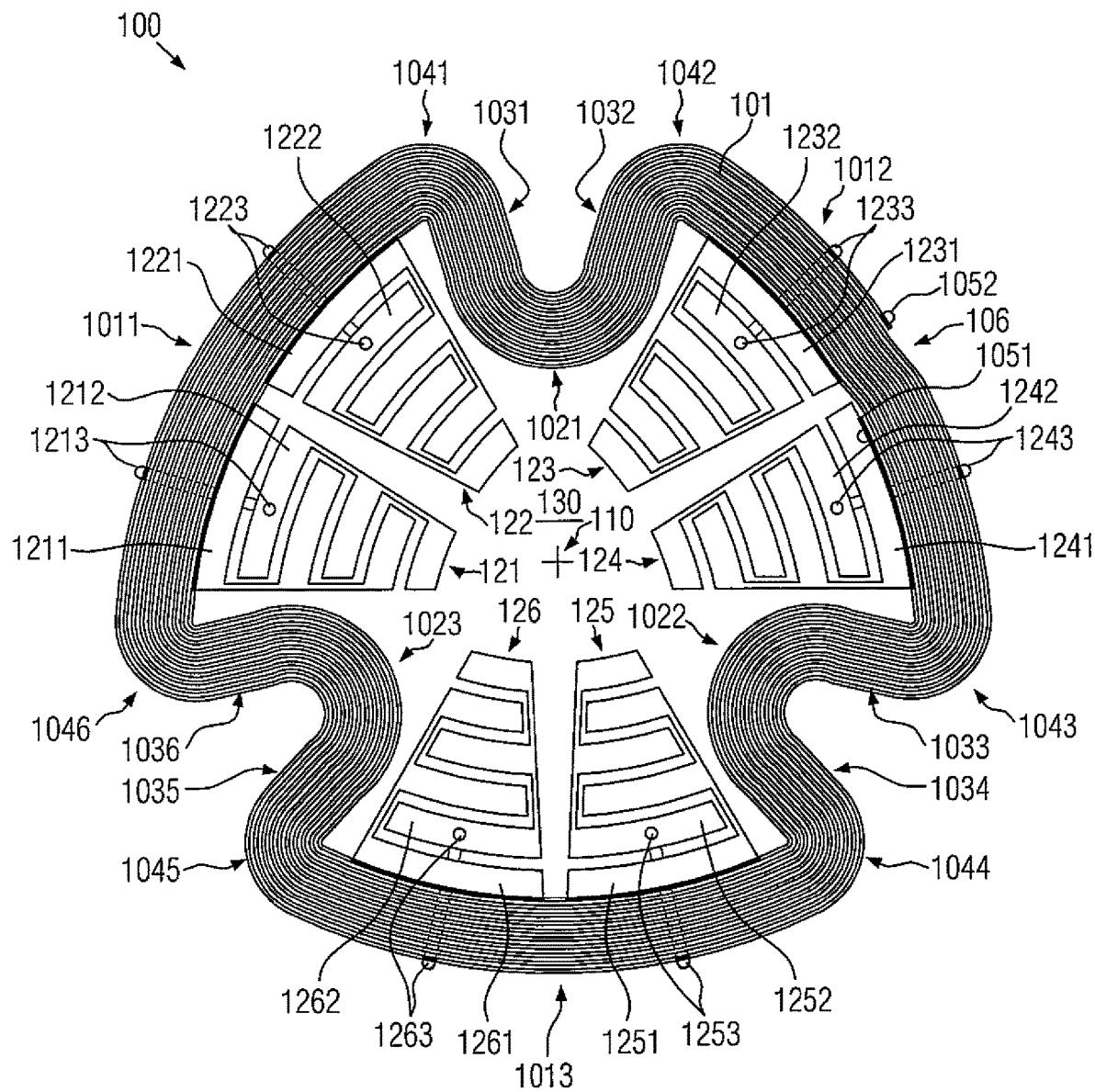

| | | |
|---|---|---|
| FR | 3001376 | 8/2014 |
| FR | 3001377 | 8/2014 |
| FR | 3001377 A1 | 8/2014 |
| FR | 3001378 A1 | 8/2014 |
| RU | 2508200 | 10/2012 |
| WO | 2008/027996 | 3/2008 |

OTHER PUBLICATIONS

Canadian Office Action dated Mar. 6, 2018 for Application No. 2,966,063 which issued in related case.
Chinese Office Action, including English translation, dated Jan. 26, 2018 for Application No. 201580065449.9 which issued in related case.

PASSIVE SENSING MEANS FOR A PHYSIOLOGICAL PARAMETER MONITORING SYSTEM

FIELD OF THE INVENTION

The present invention relates to the field of physiological parameter monitoring systems, in particular for monitoring variations of intraocular pressure. The invention relates in particular to a passive sensing means for use in a physiological parameter monitoring system and to a corresponding physiological parameter monitoring system.

BACKGROUND OF THE INVENTION

Intraocular pressure is one of the physiological parameters that allows diagnosis and monitoring of eye diseases such as glaucoma. Recently, portable and non-invasive sensing means and methods have been developed in order to measure daily variations of a patient's intraocular pressure, avoiding invasive surgical procedures where sensing means would need to be implanted in a patient's eye. Furthermore, the portability of non-invasive systems has the advantage that patients are no longer required to be immobilized at a hospital or clinic, but that the physiological parameters can now be continuously monitored in daily life situations.

Non-invasive sensing means known in the art usually comprise a sensing device that can be incorporated in a carrier device, such as a contact lens, which will be carried by a patient for monitoring purposes. Furthermore, the non-invasive sensing device can be used in combination with an external monitoring system that can receive and analyze data from the sensing means.

Different types of non-invasive sensing means for contact lenses are known, among which active sensors using miniaturized low power electronics such as microchips, active strain gages and the like, and therefore requiring an energy source. WO 2011/083105 A1 discloses for instance an active sensor comprising concentric strain gages and an associated microprocessor incorporated in a contact lens.

In contrast thereto, purely passive sensors have been developed in order to avoid using an energy source that might cause discomfort to a patient, for instance due to the generation of radiation in close vicinity of or even in direct contact with the patient's eye. A passive sensor is known from EP 2 412 305 A1, disclosing a portable physiological parameter monitoring system comprising a resonant LC circuit incorporated in a soft contact lens, wherein the resonant LC circuit responds to an external magnetic field generated by a complementary portable device, as known from instance from EP 2 439 580 A1, as well as a base station for analyzing the data acquired by the portable device. This type of passive sensor is known to rely on variations of the resonance frequency of the LC circuit incorporated in the contact lens as a function of variations of the intraocular pressure, as the latter should affect the shape of the surface of the eye and, consequently, also of the soft contact lens resting thereon. In turn, deformations of the soft contact lens should modify a capacitance of the resonant circuit.

However, the integration of sensors, passive or active, in contact lenses has been found to be more complex and more expensive than expected, preventing thus far a commercialization of portable intraocular pressure monitoring systems. A recurrent problem is that sensors are usually manufactured flat and subsequently bent to adopt the spherical cap shape of the over-molded lens, which has been found to create deformed areas in the final lens, for instance rippled edges, and sometimes also misalignments between the electrical components of the sensor. Thus, further to not being comfortable for wearing the lens, these deformations prevent a proper flat placement of the lens against the surface of the eye. As a consequence, the necessary sensitivity of the system to deformations of the surface of the eye cannot be reached.

WO 2009/111726 A2 discloses a surface deformation sensor comprising a contact lens formed by an external rigid layer and an internal soft layer bounded together at their edge, with a gap between the rigid and the soft layers. WO 2009/111726 A2 further discloses a resonant LC circuit formed by an inductive coil and a sensing capacitor, wherein the inductive coil and an upper electrode of the capacitor are included in the rigid layer and electrically connected to a lower electrode included in the soft layer. However, the fabrication of this type of surface deformation sensor requires various complex steps of integrating circuit components both in the rigid and in the soft layers, as well as the integration of a mechanism for electrically connecting the two layers.

Thus, an objective of the present invention is to provide an improved passive sensor that can be incorporated in a contact lens of a physiological parameter monitoring system, and a corresponding physiological parameter monitoring system, without the aforementioned problems. In particular, the passive sensor and corresponding monitoring system should also respect common requirements of comfort of wearing and, as much as possible, unimpaired vision of the subject wearing the lens with integrated passive sensor. An objective of the present invention is also to provide a passive sensor that improves the placement of the contact lens against the surface of an eye and responsiveness of the physiological parameter monitoring system to surface deformations.

GENERAL DESCRIPTION OF THE INVENTION

According to an aspect of the invention, the objective is solved with a passive sensing means according to claim 1 or claim 2 for a contact lens of a physiological parameter monitoring system for detecting variations of a physiological parameter. The passive sensing means, which can be for detecting variations of intraocular pressure, forms a resonant circuit comprising an inductor and at least one capacitor. According to a first aspect, the inductor and said at least one capacitor are coplanar in one layer. According to a second aspect, the passive sensing means, and in particular the inductor and/or said at least one capacitor, forms first electrodes of at least one sensing capacitor. These two aspects can be taken independently or combined with each other and both solve the aforementioned objective, as explained hereafter.

The use of coplanar conductive, inductive and/or capacitive, elements in the passive sensing means provides with a specific and advantageous geometry of the electric field lines generated therein, especially in comparison to passive sensors known in the art having sensing capacitive elements with a substantially face-to-face parallel electrode configuration or with their electrodes arranged on two different layers or planes of the contact lens. Indeed, because of the coplanar circuit elements, the electric field lines can protrude out of the plane of the inventive passive sensing means. Therefore, parasitic capacitances can exist with other surrounding materials having a high relative permittivity when a layer of a low relative permittivity is provided in-between.

In particular, the present invention takes advantage of the high relative permittivity of eye tissue and/or of the tear film thereon in order to provide at least one sensing capacitor for detecting variations of the surface of the eye, as will become more obvious with the description of the embodiments.

In fact, the coplanar elements of the inventive passive sensing means, in other words the inductor and/or the at least one capacitor, form first electrodes of sensing capacitors using the parasitic capacitances existing with the underlying surface of the eye and/or tear film thereon when the passive sensing means is attached to a contact lens placed on the eye. In other words, instead of having a physically built-in second sensing electrode in the radial direction towards the eye surface, which would—theoretically—vary following the deformations of the surface of the eye but is in practice less efficient than expected, the inventive passive means provides "physically" only for first sensing electrodes, as its configuration and resulting electric field lines enable that the actual surface of the eye and/or the tear film thereon becomes the second sensing electrodes. Thus, an advantage compared to passive sensing means known in the art is that the present invention does not need any physically built-in second electrodes for the sensing capacitors, as the actual surface of the eye and/or the tear film thereon, which are opposite the inductor and/or the at least one capacitor of the passive sensing means, can be the second sensing electrodes. Thus, the invention allows a more direct and efficient monitoring of the deformations of the surface of the eye than intraocular pressure sensors known in the art.

Further advantageous optional features are described in the dependent claims and will also be described hereafter.

Preferably, the inductor can be a flat inductor comprising a plurality of, preferably three, concave arc-shaped segments with respect to a substantially central point of said passive sensing means, and wherein for at least one, preferably all, of the plurality of concave arc-shaped segments, the radius of curvature of said at least one segment at a point thereof is greater than the distance between said point and said substantially central point. Here, by the expression "arc-shaped", it should be understood that each arc-shaped inductor segment has, respectively, a curved geometry that follows essentially the shape of an arc of an ellipse, in particular an arc of a circle. Furthermore, while each arc-shaped segment can preferably be a continuous arc-shaped segment, a plurality of shorter back-to-back linear segments could also realize one longer segment having a globally arc-shaped geometry, which would also allow carrying out the invention. Also, by the expression "concave with respect to a substantially central point" and the like, it should be understood that the arc-shaped segments are all concave with respect to a same reference point of the passive sensing means, which can be about the geometrical center thereof, but which is not the center of any of the arc-shaped segments. Thus, according to the invention, the concave arc-shaped segments are not on a circle centered on this reference substantially central point.

Thus, in a preferred embodiment, the inventive passive sensing means can have an inductive element with a structure comprising a plurality, preferably three, flap or ear-like segments that can be better adapted to the concave cap shape of a contact lens than inductors of known sensors because they allow controlling the areas of the passive sensing means that will be bent, folded and/or plastically deformed during the incorporation or attachment to a lens. Given the dimensions of contact lenses and therefore the requirements on the dimension of passive sensing means, three concave arc-shaped inductor segments can provide a better compromise in terms of sensitivity and surface coverage, as well as in terms of flexibility for the incorporation of the sensor in a contact lens than more or less such segments. However, two, four or more concave arc-shaped segments with large radii should not be ruled out in variants of preferred embodiments. Furthermore, the curvature radii of the concave arc-shaped segments of the inductor can advantageously be chosen such that, once the passive sensing means is deformed for its incorporation in a contact lens, they will essentially describe segments of a same predetermined circle of the contact lens, which allows easier placement in the contact lens.

In a variant of a preferred embodiment, the inductor can further comprise convex arc-shaped segments arranged between the concave arc-shaped segments. Here, the expression "convex arc-shaped segments" should be understood in a manner similar to "concave" as explained above. Thus, the convex arc-shaped segments are convex with respect to a substantially central point of the passive sensing means, as explained above. In this way, the areas where the passive sensing means can be bent during an incorporation or attachment process to a contact lens can be controlled.

In a further variant, the inductor can further comprises straight segments joining said convex arc-shaped segments to said concave arc-shaped segments, and the junctions between said straight segments and the concave arc-shaped segments can preferably be rounded. The length of the joining straight inductor segments can be used to better control the amount of material between the concave arc-shaped segments. Rounded junctions between successive inductor segments provide smoother shapes than rough pointy edges and are thus easier to attach to the concave cap shape of a contact lens. Here, attention should be brought to the fact that, while in this variant the rounded junctions could thus be concave-shaped, they are however not concave "with respect to the center point", unlike the "concave arc-shaped segments" as explained above.

In alternative embodiments, the inductor can be ring-shaped and circular. This variant can be advantageous to increase the amplitude of the signal at the antenna of the complementary portable device generating the external magnetic field.

Preferably, the inductor can be a spiral inductor. Thus, a flat structure can be manufactured by depositing a conductive material in or on a carrier substrate following a spiral. Advantageously, the inductor can comprise 5 to 20 spires, preferably 8 to 15 spires, more preferably 10 to 13 spires. Also, in preferred embodiments of this variant, the width of the spires and/or the distance between spires can be in a range from about 30 µm to about 100 µm, preferably about 40 µm to about 80 µm. Thus, the invention allows combinations of number of spires and dimensions that can advantageously allow a subject wearing a contact lens with the inventive passive sensing means to keep a clear vision. In particular, it is possible but not necessary that the width of the spires and the distance between successive spires are the same. Advantageously, the width of the inductor can be about 2 mm or less, preferably about 1.5 mm or less. The width of the inductor can in fact be greater than this value, but it is more advantageous that it is kept lower in order to keep the subject's vision clear.

Preferably, said at least one capacitor can be a coplanar capacitor. Coplanar circuit elements are advantageous for achieving a flat passive sensing means, as they will provide with a specific electric field line geometry that allows taking advantage of the high relative permittivity of eye tissue and/or the tear film thereon for monitoring deformations of the surface of the eye.

Preferably, said at least one capacitor can be provided at an inner circumference of the inductor, in particular towards a central area of the passive sensing means. Thus, while the inductor can provide for first electrodes of sensing capacitors on circumferential areas of the surface of the eye, the at least one physical capacitors can provide for first electrodes of sensing capacitors covering a surface within an inner circumference of the inductor, preferably over the cornea.

In an advantageous variant of a preferred embodiment, for at least one, preferably all, of the plurality of inductor concave arc-shaped segments, at least one capacitor can be provided at an inner circumference of said inductor concave arc-shaped segment towards a central area of said passive sensing means. This arrangement was found advantageous for bending the passive sensing means in view of its attachment to a contact lens. While it is possible that the passive sensing means works with only one capacitor, it is more advantageous in terms of sensitivity to include more than one capacitor. In a preferred variant, it is therefore possible to provide at least one capacitor at an inner side of each inductor concave arc-shaped segment. A configuration with two capacitors for each of the inductor concave arc-shaped segment was found even more advantageous in terms of sensitivity and surface coverage, while providing for sufficient visibility for a subject wearing a contact lens with the inventive passive sensing means.

In a further variant, said at least one capacitor can be larger towards the inner circumference of the inductor towards said central area. In preferred embodiments, a trapezoidal-like geometry of said at least one capacitor was found advantageous, as it can be easily bent to follow the concave cap geometry of a contact lens. The latter geometry was found advantageous in particular in combination with a circular ring-shaped inductor.

In another variant, said at least one capacitor can be partially arc-shaped following the convex arc-shaped segments at its extremity towards the central area. Thus, the geometry of capacitors, especially of coplanar capacitors, can advantageously be adapted to that of the inductor in order to increase the coverage of the surface of an eye, while still leaving at least a central zone free to allow for a sufficiently unimpaired vision.

Preferably, said at least one coplanar capacitor can comprise a first electrode and a second electrode, wherein said first electrode can be electrically connected to an inner circumference of said inductor and said second electrode can be electrically connected, in particular by means of an electrically conductive via, to an outer circumference of said inductor. While the actual sensing elements are provided in a coplanar manner, it is still possible to use electrically conductive vias for the electrical connections between the terminals of the circuit components. It is also possible to provide the first electrode of each capacitor as an extension of the spire on the inner circumference of the inductor. In other words, the first electrode of each capacitor can be integral with the inductor.

Preferably, said at least one capacitor and/or said first electrode and second electrode can be interdigitated. Following preferred variants, an interdigitated capacitor can have its electrodes interdigitated radially and/or circumferentially. In particular, the two electrodes of a coplanar capacitor could be interdigitated with one another radially, or a first electrode could itself be interdigitated while being circumferentially coplanar with the second electrode. Interdigitated capacitors, which can also be coplanar, or more in general capacitors with interdigitated electrodes, were found advantageous to improve the sensitivity of the passive sensing means, while also providing an advantageous geometry of the electric field lines.

Preferably, the passive sensing means can further comprise a central area free of inductor and/or capacitor material. Thus, a subject can keep a substantially clear vision while wearing a contact lens with the inventive passive sensing means. The central area can be an area corresponding roughly to the average dimensions of the human pupil.

Preferably, the passive sensing means can further comprise a layer of a carrier substrate in or on which said inductor and said at least one capacitor are provided, in particular in a coplanar manner. In a variant or in addition thereto, the passive sensing means can further comprise a layer of a coating material over said inductor and said at least one capacitor and/or over the carrier substrate layer. The coating layer can be advantageous for protecting the circuit components, for instance from corrosion due to prolonged exposure to tears. Furthermore, the carrier substrate and/or the coating can preferably be removed following preferred contours of the passive sensing means. The problem of incorporating or attaching the passive sensing means to a contact lens is somewhat similar to wrapping a 3D surface with a 2D sheet. It is therefore advantageous to remove areas of carrier substrate that would create unnecessary material and therefore form ripples when deforming the passive sensing means to give it a curved shaped prior to its incorporation or attachment to a contact lens. It is in fact preferable to remove as much carrier substrate as possible in order to make the passive sensing means as flexible as possible prior to its incorporation in a contact lens, while still leaving sufficient carrier substrate material in fragile areas, which could be subject to possible tears when the passive sensing means is bent.

According to another aspect of the invention, the objective is also solved with a physiological parameter monitoring system according to claim 16. The Physiological parameter monitoring system, which can be for detecting variations of intraocular pressure, comprises a first lens element with an inner surface and an outer surface opposite the inner surface, wherein at least the outer surface is adapted for contacting an ocular tissue, in particular eyelid tissue, and wherein, preferably, the inner surface is adapted for contacting at least the cornea and/or a tear film thereon, preferably the cornea and sclera and/or a tear film thereon. Preferably, the first contact lens element provides an intermediate space between its inner surface and the surface of an eye when the peripheral area is contacting the sclera. The physiological parameter monitoring system further comprises a passive sensing means according to the previous aspect or any of its variants.

Thus, the physiological parameter monitoring system comprises the advantages of the passive sensing means according to the first aspect of the invention. In particular, the passive sensing means according to the first aspect of the invention, provides for first electrodes of at least one sensing capacitor, and the intermediate space can be an intermediate dielectric such that the surface of the eye or the tear film thereon forms second electrodes of the sensing capacitors.

Preferably, the passive sensing means can be provided at the inner surface of the first contact lens element. Whether attached to the internal optical surface of a rigid contact lens, in particular a rigid scleral contact lens, or accommodated in a recess therein, the present invention does not require complex steps of incorporation of the passive sensing means within the lens material, or of over-molding contact lens layers on the passive sensing means.

In preferred variants of advantageous embodiments, the physiological parameter monitoring system can further comprise a second lens element, preferably of a flexible material, in particular a flexible polymer material, more in particular a hydrophilic flexible polymer material, having an inner surface and an outer surface opposite the inner surface, wherein at least the inner surface can be adapted for contacting an ocular tissue, in particular at least the cornea and/or a tear film thereon, and wherein the first lens element and the second lens element can be attached to one another at a peripheral attachment area, thereby enclosing an intermediate space. Thus, the inventive system can take better advantage of a multilayered contact lens than surface deformation sensors known in the art. Indeed, the inventive passive sensing means is incorporated or attached only to the rigid part of a multilayered contact lens, thereby advantageously avoiding to have to incorporate or attach any circuit element to the soft layer of the lens, which improves the flat placement of the soft layer against the surface of an eye in comparison to systems known in the art, as the soft layer no longer integrates stiffening elements. Thus, the formation of ripples is also avoided in the soft layer. In addition, the integration of a mechanism for electrically connecting circuit elements in the soft layer to circuit elements in the rigid layer is also avoided with the inventive passive sensing means.

Thus, depending on the variant, it is even possible to use only a rigid contact lens, in particular a rigid scleral contact lens, without any soft contact lens layer, as the inventive passive sensing means with circuit elements arranged in a coplanar manner can even allow a detection of surface deformations without using a soft contact lens layer as sensing layer. In other variants, also depending on the resonance frequency, using a multilayered contact lens as described above can be more advantageous. In all variants, the contact lens(es) can be corrective or not.

In a variant, when the physiological parameter monitoring system comprises a multilayered contact lens, the intermediate space can be filled with a dielectric material. It is then also preferable that the dielectric material be compressible such that, when the second lens element is flexible, deformations of the underlying surface can still be detected. In fact, following preferred variants, the intermediate space could be fully filled with a compressible dielectric material or partially filled with a mixture of compressible and incompressible dielectric materials, such that the deformations of the underlying surface can be detected. Although multilayered contact lenses known in the art usually enclose an intermediate space filled with air, it is always possible to fill said space with another dielectric material, preferably having also a low relative permittivity. In particular, the dielectric material can have a relative permittivity value, $\varepsilon_r$, of less than the relative permittivity of a tear film and/or an ocular tissue at ambient temperature, preferably less than about 10 times the relative permittivity of a tear film and/or ocular tissue at ambient temperature, more preferably a relative permittivity value, $\varepsilon_r$, between about 1 and about 5. Advantageously, decreasing the relative permittivity can increase the sensitivity.

Advantageously, in a variant of a preferred embodiment, the second contact lens element can be a soft contact lens, in particular extending at least over the cornea. Thus, it is even possible to use directly a corrective or non-corrective soft contact lens and attach the same to the first contact lens element, which avoids further complex steps of manufacturing dedicated soft layers. An advantage thereof is that using directly existing soft contact lenses can avoid also completely the problem of ripple formation and flat placement against at least the cornea. This variant was found to be particularly adapted for monitoring deformations of the surface of the eye, and therefore also variations of the intraocular pressure.

In preferred variants of advantageous embodiments, the second contact lens element can extend over the cornea and part of the sclera leaving a non-contact area at the limbus. Most soft so-called corneal contact lenses are in fact also partially scleral and can therefore also be used in this variant. Leaving a non-contact area at the limbus of the eye can provide for a small depression allowing the second lens element, in this variant for instance a soft layer, in particular a soft contact lens, to stick flat against the surface of at least the cornea with help of the tear film.

LIST OF FIGURES

Figure 2:
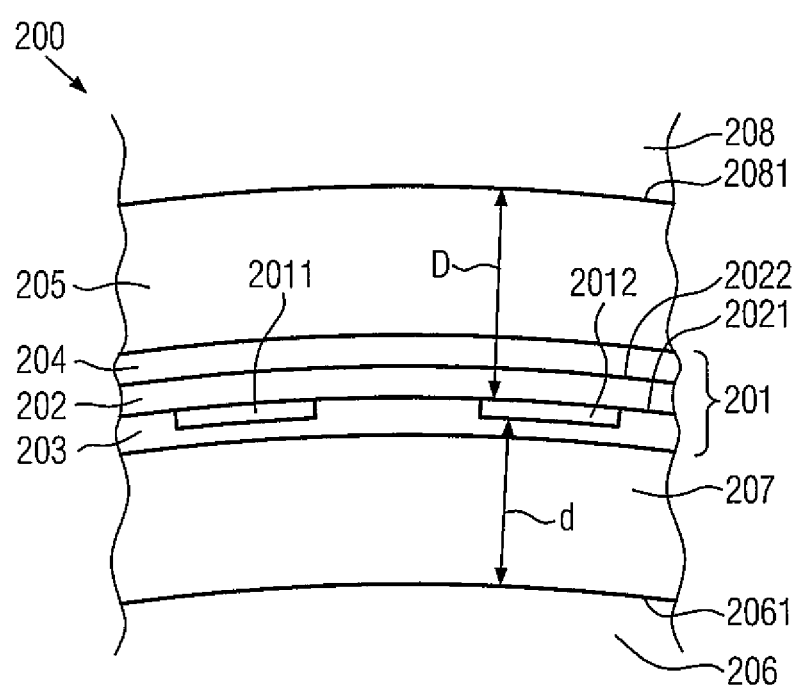
Figure 3:
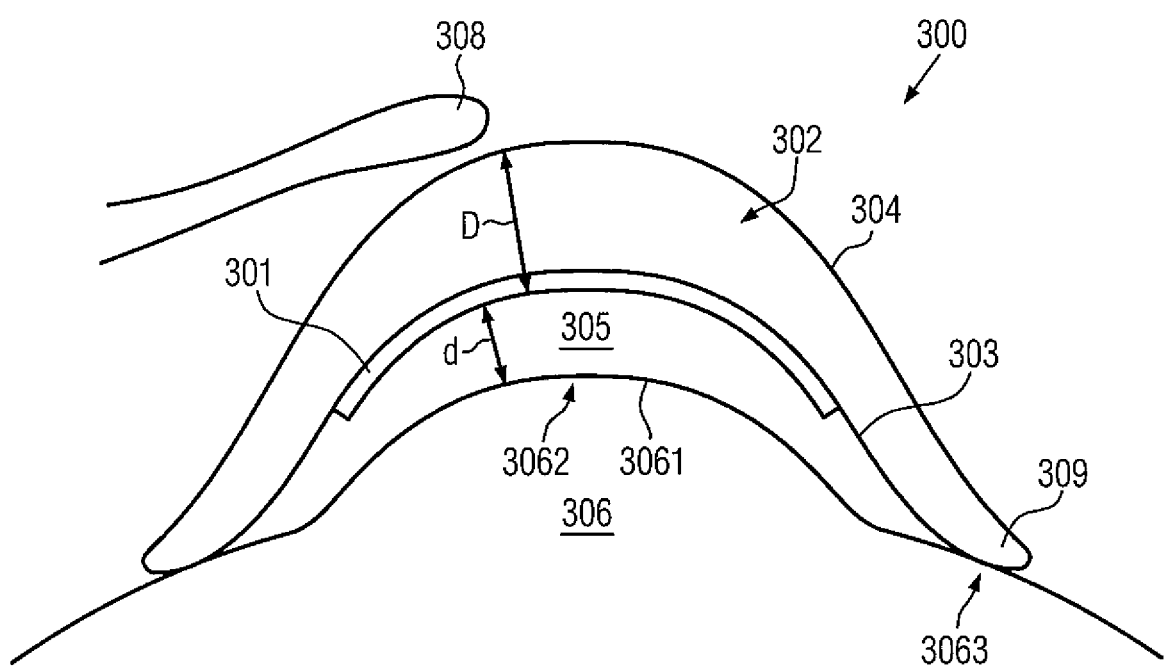
Figure 4A:
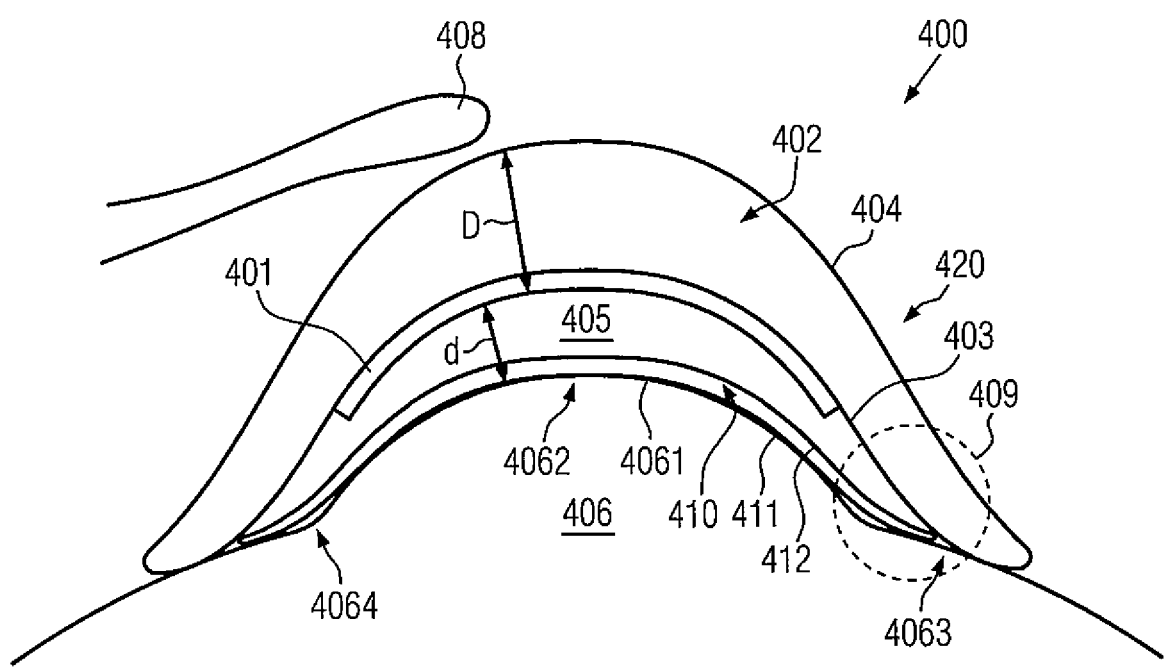
Figure 4B:
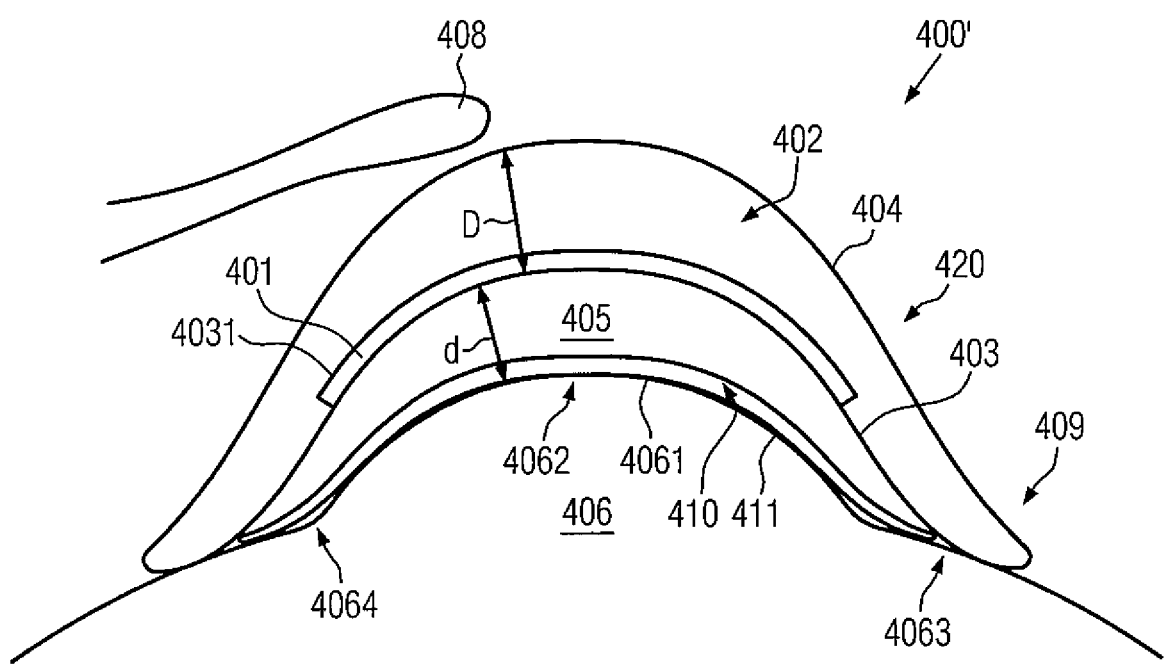
Figure 5:
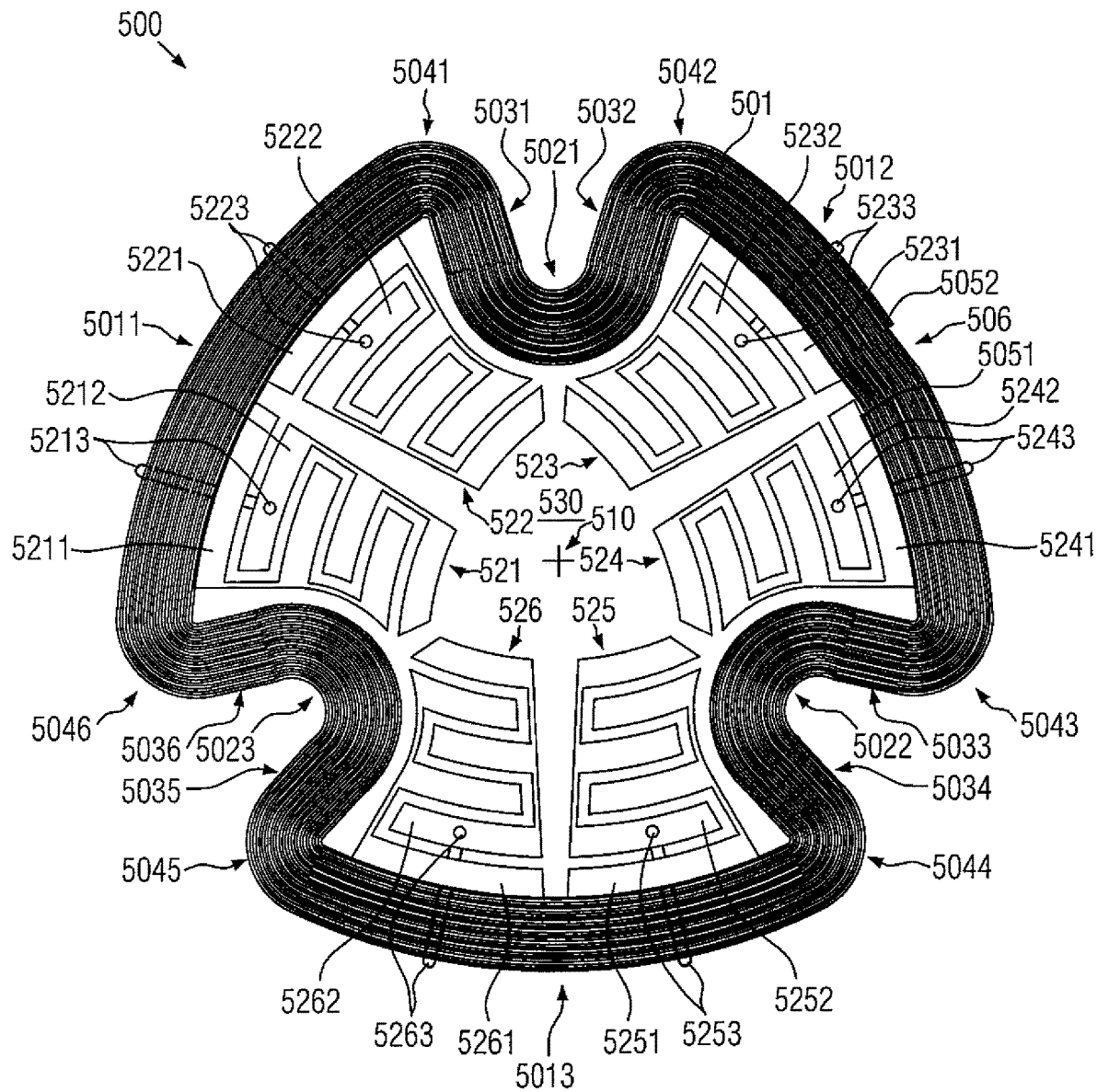
Figure 6:
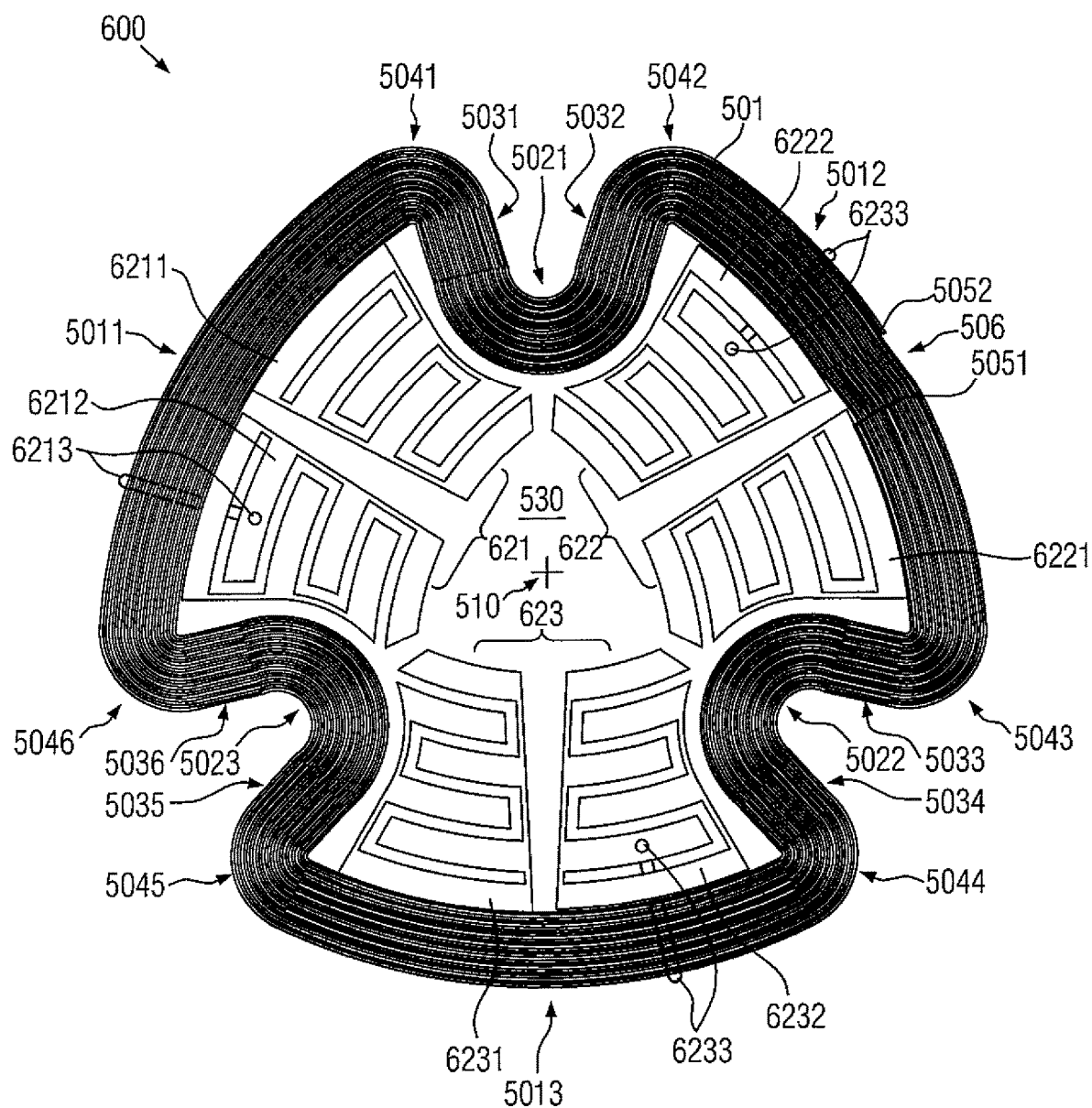
Figure 7:
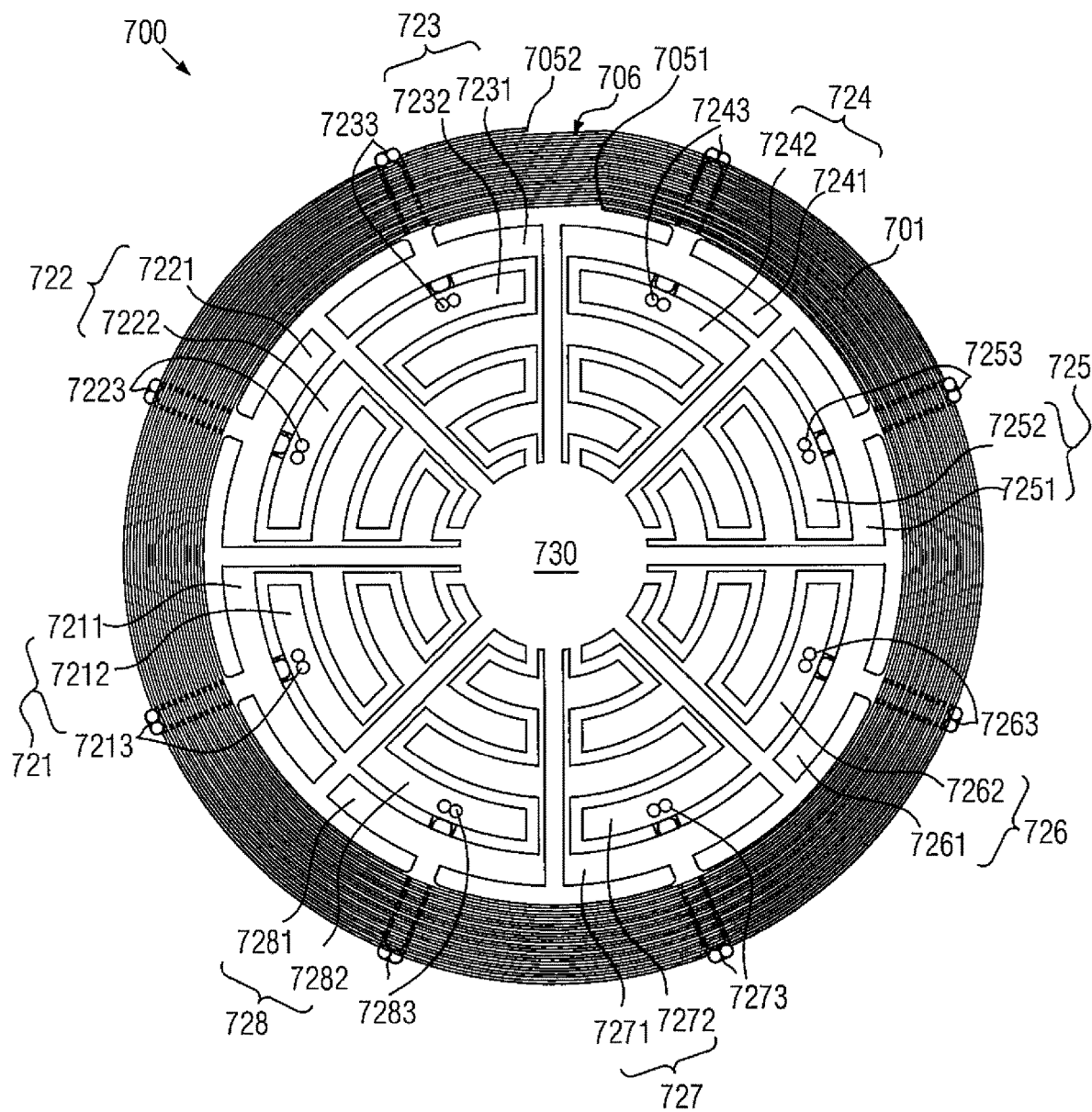
Figure 8:
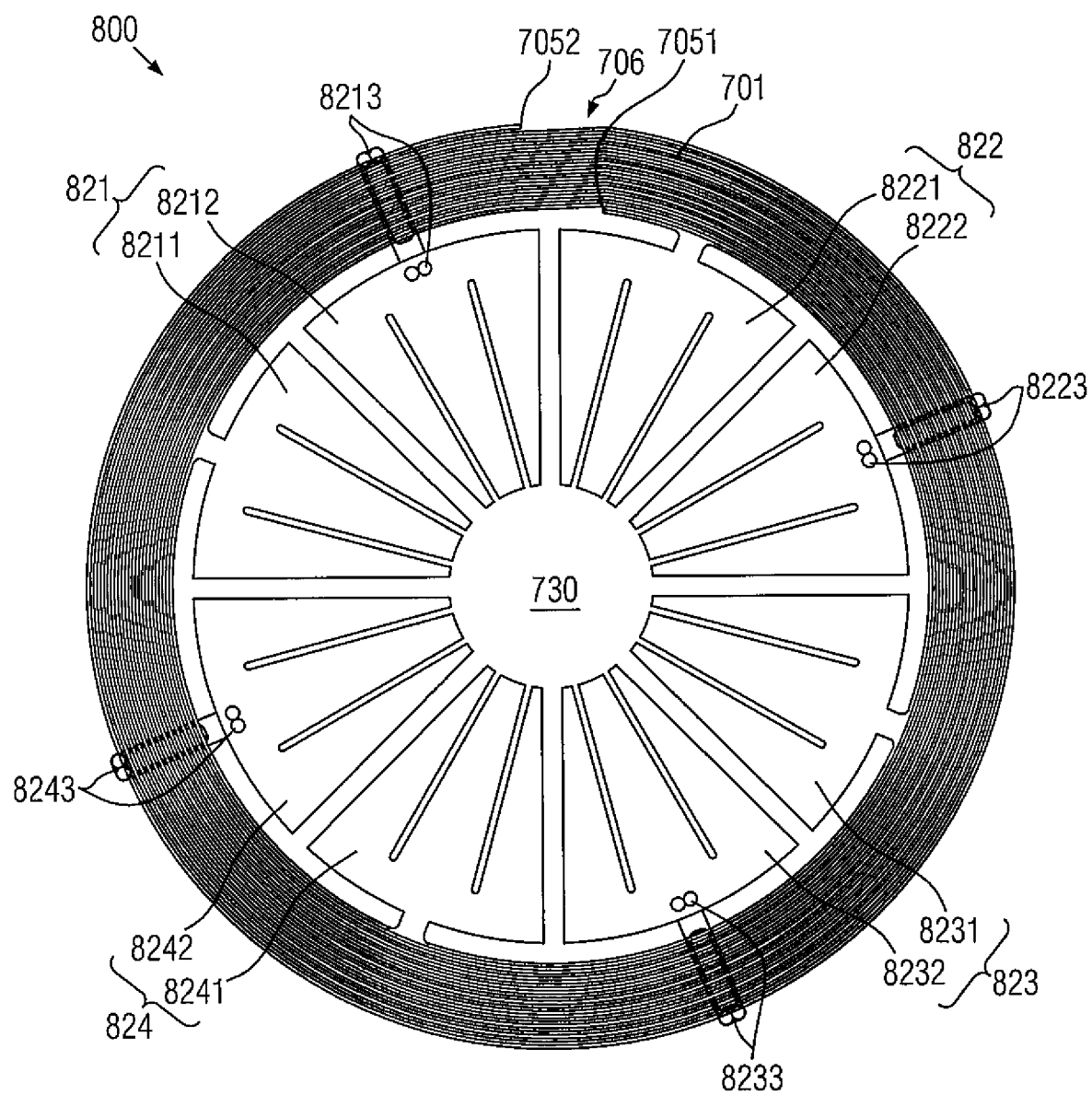

The invention will be described in more detail in the following, based on advantageous embodiments described in combination with the following figures:

FIG. 1 schematically illustrates an exemplary embodiment of a passive sensor according to an aspect of the invention;

FIG. 2 schematically illustrates an exemplary embodiment of a physiological parameter monitoring system according to another aspect of the invention;

FIG. 3 schematically illustrates a variant of the physiological parameter monitoring system illustrated in FIG. 2, in another exemplary embodiment;

FIG. 4A schematically illustrates a further variant of the physiological parameter monitoring system illustrated in FIG. 2, in another exemplary embodiment;

FIG. 4B schematically illustrates a variant of the physiological parameter monitoring system illustrated in FIG. 4A, in another exemplary embodiment;

FIG. 5 schematically illustrates a variant of the passive sensor illustrated in FIG. 1, in a further exemplary embodiment;

FIG. 6 schematically illustrates another variant of the passive sensors illustrated in FIGS. 1 and 5, in a further exemplary embodiment;

FIG. 7 schematically illustrates another exemplary embodiment of a variant of a passive sensor according to an aspect of the invention; and FIG. 8 schematically illustrates a variant of the passive sensor illustrated in FIG. 7, in another exemplary embodiment.

DESCRIPTION OF EMBODIMENTS

FIG. 1 illustrates a passive sensing means 100 for a contact lens, which can be used in a physiological parameter monitoring system, for instance those detailed in the embodiments with reference to FIGS. 2 to 4B, in an exemplary embodiment of the first aspect of the invention. In this embodiment, the passive sensing means 100 is a resonant circuit for use in a contact lens for detecting variations of a physiological parameter when the contact lens is being worn. In particular, the passive sensing means 100 can be used in a contact lens for monitoring variations of the intraocular pressure, for instance for patients suffering from glaucoma.

As can be seen in FIG. 1, the passive sensor 100 comprises an inductive element, here inductor 101, and at least one capacitive element, here the plurality of capacitors 121, 122, 123, 124, 125 and 126, which are all coplanar. In other words, prior to subsequent steps of incorporation in a contact lens, the passive sensor 100 is substantially flat such that it forms only one sensing layer, also when it is deformed, in particular bent, and attached to a contact lens of a physiological parameter monitoring system. For instance, the passive sensor 100 can be provided on a layer of a carrier substrate, with or without protective coating layers thereon, provided that the inductor 101 and the capacitors 121, 122, 123, 124, 125, 126 are provided in a coplanar manner.

Following a preferred variant, the inductor 101 of the embodiment illustrated in FIG. 1 is a flat inductive element, which can comprise a plurality of segments 1011, 1012, 1013 that are arc-shaped and concave with respect to a reference point, here the substantially central point 110 of the passive sensor 100, wherein this central point 110 does not need to be the geometric center of the sensor but can be close to it. As further illustrated in FIG. 1, these segments 1011, 1012, 1013 are in fact not centered on said substantially central point 110. Indeed, at least one segment 1011, 1012, 1013, and preferably all three segments 1011, 1012, 1013, has a curvature radius at a point thereof that is greater than the distance of said point to the substantially central point 110. Thus, following a preferred variant, the centers of the concave arc-shaped inductor segments 1011, 1012, 1013 can in fact be even outside the perimeter of the inductor 101. The inductor 101 then has the advantage that the flap-like or ear-like structure of the three segments 1011, 1012, 1013 will be easier to attach or to incorporate to the concave cap shape of a contact lens. In fact, it will be even possible to bend the sensor 100 such that the segments 1011, 1012, 1013 can substantially align on the same circle in the contact lens.

As also illustrated in FIG. 1, in order to further facilitate the attachment or incorporation process of the passive sensor 100 in a contact lens, in particular to better control the areas that will bend during this process, the inductor 101 of the passive sensor 100 can further comprise inwards orientated, in other words convex with respect to the substantially central point 110, arc-shaped segments 1021, 1022, 1023 joining the concave segments 1011, 1012, 1013 to one another. Depending on the desired size of the passive sensor 100, FIG. 1 also illustrates that it is possible to join the concave segments 1011, 1012, 1013 to the convex segments 1021, 1022, 1023 via straight inductor segments 1031, 1032, 1033, 1034, 1035, 1036. Thus, the depth of the inwards pointing ear-like segments 1021, 1022, 1023 can be adjusted, thereby controlling the areas that will be bent during the attachment or incorporation process in a contact lens. FIG. 1 also illustrates an advantageous variant in which the junctions 1041, 1042, 1043, 1044, 1045, 1046 between the straight segments 1031, 1032, 1033, 1034, 1035, 1036 and the concave segments 1011, 1012, 1013 are rounded in order to provide a smoother shape.

Following yet another preferred variant, the inductor 101 can also be a flat spiral inductor. In the embodiment illustrated in FIG. 1, the inductor 101 spirals from a first terminal 1051 on its inner periphery, corresponding here to that of concave arc-shaped segment 1012, towards a second terminal 1052 on the outer periphery thereof. In order to obtain a segment 1012 essentially arc-shaped, the area 106 between the two terminals 1051, 1052 can present the small deflection illustrated in FIG. 1. The inductor 101 can further comprise a succession of spires, for instance about 5 to 20 spires, preferably 8 to 15 spires, more preferably 10 to 13 spires. In the embodiment illustrated in FIG. 1, the inductor 101 comprises for instance 10 spires.

Furthermore, following another preferred variant, since it is desirable that the total width of the inductor 101 in a radial direction, that is for instance with respect to central point 110, is kept below about 2.0 mm, for instance at about 1.5 mm or even below, in the embodiment illustrated in FIG. 1, the width of a spire can be about 60 μm, while the distance between successive spires could be about 75 μm. However, in other embodiments, the width of the spires and/or the distance between successive spires could be chosen in a range from about 30 μm to about 100 μm, preferably between about 40 μm and about 80 μm. In some embodiments, they could even be the same. For instance, it would be possible to have 15 spires with a width of about 50 μm and with a distance therebetween of also about 50 μm.

As further illustrated in FIG. 1, in contrast to capacitors with a face-to-face parallel electrode configuration, the capacitors 121, 122, 123, 124, 125, 126 are coplanar capacitors, meaning that their respective electrodes 1211 and 1212, 1221 and 1222, 1231 and 1232, 1241 and 1242, 1251 and 1252, and 1261 and 1262, are coplanar to one another, at least before bending or deforming the sensor 100 for its attachment to a contact lens. As explained above, the coplanar capacitors 121, 122, 123, 124, 125, 126 are therefore also coplanar with the spiral inductor 101. In particular, the electrodes 1211, 1212, 1221, 1222, 1231, 1232, 1241, 1242, 1251, 1252, 1261, 1262 are provided coplanar with the inductor 101, for instance on a same plane, in particular a same front side, of a carrier substrate (not illustrated for clarity purposes), as will become more evident in the embodiment referring to FIG. 2. Thus, electric field lines between two respective coplanar electrodes 1211 and 1212, 1221 and 1222, 1231 and 1232, 1241 and 1242, 1251 and 1252, 1261 and 1262 can also form arcs protruding out of the plane.

Furthermore, following an advantageous variant, the capacitors 121, 122, 123, 124, 125, 126 can also be interdigitated capacitors, as illustrated in FIG. 1. Thus, a given capacitor can comprise two essentially E-shaped electrodes facing each other such that their branches are interdigitated with one another. For instance, in FIG. 1, capacitor 121 comprises two essentially E-shaped coplanar and interdigitated electrodes 1211 and 1212. Similarly, the other capacitors 122, 123, 124, 125 and 126 are also provided in this manner.

Also following an advantageous variant, at least one capacitor is provided for each of the concave arc-shaped inductor segments 1011, 1012, 1013, at their inner periphery towards the central point 110. In the embodiment illustrated with reference to FIG. 1, following a preferred variant, two capacitors are provided for each concave arc-shaped inductor segments 1011, 1012, 1013. For instance, capacitors 121 and 122 are provided in segment 1011, while capacitors 123 and 124 are provided in segment 1012, and capacitors 125 and 126 are provided in segment 1013. Following a preferred variant, first electrodes of a given capacitor 121, 122, 123, 124, 125, 126, here electrodes 1211 and 1221, 1231 and 1241, and 1251 and 1261, can be electrically connected to an inner side—or inner circumference—of the inductor 101, here to the innermost spire of segments 1011, 1012 and 1013, respectively. In turn, second electrodes, here electrodes 1212 and 1222, 1232 and 1242, and 1252 and 1262, can be connected to an outer side—or outer circumference—of the inductor 101, here to the outermost spire of segments 1011, 1012 and 1013, respectively. While the first electrodes 1211, 1221, 1231, 1241, 1251, 1261 can be provided substantially as extensions of the innermost spire of inductor 101 towards the central point 110, the second electrodes 1212, 1222, 1232, 1242, 1252, 1262 can be connected to the outermost spire of the inductor 101 by means of respective electrically conductive vias 1213, 1223, 1233, 1243, 1253, 1263. For manufacturing reasons, these vias 1213, 1223, 1233, 1243, 1253, 1263 or electrical connections can be provided on a different plane, in particular a different side, of a substrate carrying the coplanar inductor 101 and capacitors 121, 122, 123, 124, 125, 126, provided that the passive sensor 100 is globally flat. As illustrated in FIG. 1, the electrically conductive vias 1213, 1223, 1233, 1243, 1253, 1263 can comprise, respectively, a conductive bridge and can cross the substrate and, if necessary, also the second electrodes 1212, 1222, 1232, 1242, 1252, 1262.

In the embodiment illustrated with reference to FIG. 1, the capacitors 121, 122, 123, 124, 125, 126 can be larger towards the innermost spire of the inductor 101 than towards the central point 110, for instance such that the overall shape of each capacitor 121, 122, 123, 124, 125, 126 is essentially trapezoidal, with the larger base facing outwards from the central point 110 and the smaller base facing towards the central point 110. This shape can be advantageous for a subsequent bending of the passive sensor 100 in view of its incorporation in a contact lens. This shape is, however, not limitative and other shapes could be used if they facilitate the attachment of the passive sensor 100 to a contact lens or the coverage of the surface of the eye, for instance like in the embodiments illustrated in FIGS. 5 and 6.

It is also preferable to remove unnecessary material from the passive sensor 100 in order to facilitate its incorporation in a contact lens. Thus, it is advantageous to remove at least partially any unnecessary parts of the carrier substrate (not illustrated for clarity purposes), preferably following the inner and outer contours of the passive sensor 100, leaving however sufficient carrier substrate material in areas where bending the passive sensor 100 could damage the inductor 101 and/or any of the capacitors 121, 122, 123, 124, 125, 126. It is also preferable to leave a central area 130 surrounding the substantially central point 110 free of any material, for instance corresponding to the position of the pupil, such that the vision remains essentially unimpaired and the flexibility of the passive sensor 100 is improved.

FIG. 2 schematically illustrates a detail, in a cross-section, of an exemplary embodiment of a physiological parameter monitoring system 200 according to an aspect of the present invention, in particular using a passive sensing means 201 forming a resonant circuit, for detecting variations of a physiological parameter related in particular to deformations of the surface 2061 of a layer 206 of a high relative permittivity material. In a preferred variant of this embodiment, the passive sensing means 201 can be the passive sensor 100 of the embodiment illustrated with reference to FIG. 1. However, variants of the passive sensor 100 or other substantially coplanar passive sensors forming a resonant circuit could be used instead. In particular any of the passive sensors 500, 600, 700, 800 of the embodiments illustrated with reference to FIGS. 5 to 8 could be used in variants of this embodiment.

In the exemplary embodiment illustrated in FIG. 2, the passive sensing means 201 is provided as a plurality of coplanar conductive elements, which can be inductive and/or capacitive elements, forming a resonant circuit with a given resonance frequency chosen in a range of frequencies preferably adapted for a medical use. For clarity purposes, only two coplanar such elements 2011, 2012 are illustrated in FIG. 2. In a preferred variant, when the passive sensing means 201 is the passive sensor 100 of the embodiment illustrated in FIG. 1, or any of the passive sensors 500, 600, 700, 800 of the embodiments illustrated in FIGS. 5 to 8, the two coplanar conductive elements 2011, 2012 can correspond to two successive conductive elements in a cross-section, for instance two successive spires of the spiral inductor 101 or two successive branches of either of the interdigitated capacitors 121, 122, 123, 124, 125, 126. Like the embodiments illustrated in FIG. 1 and in FIGS. 5 to 8, the passive sensing means 201 of the exemplary embodiment illustrated in FIG. 2 can be provided on a layer 202 of a carrier substrate material, in particular on a front side 2021 thereof, with an optional layer 203 of a protective coating material being provided on or over the front side 2021 and/or the conductive elements 2011, 2012. Furthermore, the passive sensing means 201 can be attached to a carrier element, illustrated as the layer 205, of the physiological parameter monitoring system 200 at the backside 2022 of the layer 202 of carrier substrate material. Thus, an optional layer 204 can be provided over the backside 2022, of a coating material and/or an adhesive material.

As further illustrated in FIG. 2, the passive sensing means 201 attached to the carrier element 205 will be used to determine variations of a physiological parameter related to deformations of the surface 2061 of the first high relative permittivity layer 206. Thus, in the vicinity of the resonance frequency of the passive sensing means 201, the relative permittivity of the carrier 205 and of the layers of substrate 202, coating 203, and coating and/or adhesive 204, are preferably chosen all very low in comparison to the relative permittivity of the first layer 206, for instance preferably at least ten times lower.

The use of coplanar conductive, inductive and/or capacitive, elements 2011, 2012 provides with a different electric field lines geometry than capacitors with a face-to-face parallel electrode configuration, such that instead of having essentially straight electric field lines between two opposite parallel electrodes, the electric field lines in the coplanar configuration illustrated in FIG. 2 can also protrude out of the plane of the coplanar conductive elements 2011, 2012, for instance following arcs. It is known that parasitic capacitances can exist between the conductive elements 2011, 2012, as well as between the same and any other high relative permittivity elements in vicinity thereof, which can affect the resonance frequency of the passive sensing means 201. In the embodiment illustrated in FIG. 2, an intermediate layer 207 is provided between the passive sensing means 201 and the layer 206 of high relative permittivity, wherein the relative permittivity of said intermediate layer 207 is also very low, preferably at least ten times lower, compared to that of the material of layer 206. Thus, since electric field lines can protrude out of the plane of the coplanar elements 2011, 2012, parasitic capacitances can also be formed between each of the coplanar conductive elements 2011, 2012 of the passive sensing means 201 and opposite areas of the surface 2061 of the high relative permittivity layer 206, thereby forming a plurality of sensing capacitors having substantially a parallel electrode configuration, wherein one electrode is one of the conductive elements 2011, 2012 and the other electrode is the opposite area of the surface 2061. In other words, the conductive elements 2011, 2012 of the passive sensing means 201—for instance the spires of the spiral inductor 101 and/or the various branches of the interdigitated capacitors 121, 122, 123, 124, 125, 126—form first electrodes for a plurality of sensing capacitors, and the areas opposite thereto on the surface 2061 form respective second electrodes of these sensing capacitors, without needing to physically build any second sensing electrodes in the passive sensing means 201. The deformation of the surface 2061 of the high relative permittivity layer 206 will affect the distance between these electrodes, thereby also affecting the resonance frequency. This variation can, in turn, be detected using an external magnetic field following known methods.

If a layer 208 of another high relative permittivity material is provided for instance over the carrier 205, as illustrated schematically in FIG. 2, further parasitic capacitances could also exist between conductive elements 2011, 2012 of the passive sensing means 201 and opposite areas of the layer 208, which could perturb the monitoring of the deformations of the surface 2061 of the first high relative permittivity layer 206. Thus, it is preferable that the carrier element 205 is manufactured in such a manner that the passive sensing means 201 can be attached thereto such that the distance D from any of the coplanar conductive elements 2011, 2012 to the surface 2081 of the layer 208 is greater than the distance d from said coplanar conductive element 2011, 2012 to the opposite area of the surface 2061 of the layer 206. In this way, the parasitic capacitances of the sensing capacitors can be main parameters varying as a function of the deformations of the surface 2061, while any other capacitance of the physiological parameter monitoring system 200 will be either fixed or negligible in comparison.

In a preferred variant of the embodiment illustrated with reference to FIG. 2, in particular in a variant wherein the passive sensing means 201 is the passive sensor 100 of the exemplary embodiment illustrated in FIG. 1 or the passive sensors 500, 600, 700, 800 of any of the variants illustrated in FIGS. 5 to 8, the first high relative permittivity layer 206 can be eye tissue such as the cornea and/or a tear film formed thereon, the second high relative permittivity layer 208 can be eye tissue such as the eyelid and/or a tear film formed between the eyelid and the carrier element 205, wherein the carrier element 205 can be a contact lens, and the low relative permittivity intermediate layer 207 can be an intermediate space filled with air or, in further variants, with a biocompatible low relative permittivity dielectric material. Finally, the physiological parameter can be the intraocular pressure, which can thus be monitored following the variations of the resonance frequency as a function of the distance variation between the passive sensor 100 and the surface of the eye, in particular the cornea and/or the tear film thereon. In that preferred variant, the inductor 101 and the plurality of capacitors 121, 122, 123, 124, 125, 126 can be chosen such that the initial resonance frequency of the passive sensor 100 is in the vicinity of 30 MHz. Near this frequency, the relative permittivity $\varepsilon_r$ for the different layers could then be: $\varepsilon_r$ (eyelid)≈80 for the layer 208, and $\varepsilon_r$ (cornea) 100 and $\varepsilon_r$ (tear film)≈80, such that it could be considered that $\varepsilon_r$ (cornea)≈$\varepsilon_r$ (tear film) near 30 MHz, for the layer 206. Furthermore, the relative permittivity of the material forming the contact lens 205, which could be silicon or a polymer material that can be used for rigid or soft contact lens elements, could be $\varepsilon_r$ (silicon)≈3, and that of the dielectric material in the intermediate space 207, which could be air or another low relative permittivity biocompatible dielectric material, could be $\varepsilon_r$ (air, other dielectric)≈1-3.

FIG. 3 illustrates a preferred variant of the physiological parameter monitoring system 200 of the embodiment illustrated with reference to FIG. 2, wherein variations of the intraocular pressure can be monitored. Thus, the embodiment illustrated in FIG. 3 is in all aspects analog to the embodiment illustrated in FIG. 2. In this variant, the physiological parameter monitoring system 300 can comprise a passive sensing means 301, which can be in particular the passive sensor 100 of the embodiment illustrated in FIG. 1 or the passive sensors 500, 600, 700, 800 of any of the variants illustrated in FIGS. 5 to 8, preferably attached at its backside to the inner surface 303 of a contact lens 302, such that the coplanar inductance 101 and capacitors 121, 122, 123, 124, 125, 126 are arranged facing the surface 3061 of an eye 306, in particular of the cornea 3062, for which intraocular pressure variations will be monitored. For simplicity purposes, the passive sensing means 301 is illustrated as a single layer, but the skilled person will understand that the configuration is analog to that of the embodiment illustrated in FIG. 2 applied to the passive sensor 100 of FIG. 1 or any of the passive sensors 500, 600, 700, 800 of the embodiments illustrated with reference to FIGS. 5 to 8.

In the embodiment illustrated in FIG. 3, the contact lens 302 also comprises an outer surface 304 adapted for contacting eye tissue and/or a tear film thereon. In particular, the inner surface 303 of the lens 302 is adapted for contacting at least the surface 3061 of the eye 306 and preferably also a tear film thereon, while the outer surface 304 of the lens 302 is adapted for contacting at least the eyelid 308 and preferably also a tear film. Furthermore, the contact lens 302 can preferably be a rigid contact lens of the scleral type, such that its peripheral area 309 rests on the surface 3061, in particular on the sclera 3063 and/or on the tear film formed thereon (the tear film is not illustrated for simplicity), and such that the lens 302 further provides an intermediate space 305, which can in particular be filled with air, between the surface 3061 of the eye 306 and the passive sensing means 301. Following a preferred variant of the embodiment illustrated in FIG. 2, the distance d between the passive sensing means 301 and the surface 3061 is smaller than the distance D between the passive sensing means 301 and the outer surface 304 of the contact lens 302, for instance, without limiting the present invention to these values, d≈350 μm and D≈500 μm, such that any parasitic capacitance between the passive sensing means 301 and the eyelid 308 will be either negligible or non-existent in comparison to the parasitic capacitances of the sensing capacitors formed between the passive sensing means 301 and the surface 3061.

The variant illustrated in FIG. 3 can be particularly advantageous when the passive sensing means 301 is chosen with a low resonance frequency, for instance well below 30 MHz, at which the relative permittivity of the cornea becomes much larger than that of the tear film thereon, in other words at frequencies for which $\varepsilon_r$ (cornea)>>$\varepsilon_r$ (tear film). In that case, the tear film on the surface 3061 of the eye 306 can be considered to form part of the low permittivity intermediate space 305.

FIG. 4A illustrates another preferred variant of a physiological parameter monitoring system 400, which is in most aspects similar to the physiological parameter monitoring system 300 of the embodiment illustrated in FIG. 3. Thus, the physiological parameter monitoring system 400 is used for monitoring variations of the intraocular pressure in the eye 406, and comprises a passive sensing means 401, which can again preferably be the passive sensor 100 of the embodiment referring to FIG. 1, or any of the variants described with reference to FIGS. 5 to 8, again preferably attached at its backside to the inner surface 403 of a first rigid contact lens or contact lens element 402, such that the coplanar conductive elements of the passive sensing means 401, for instance the inductance 101 and capacitors 121, 122, 123, 124, 125, 126, are arranged facing the surface 4061 of the eye 406, in particular the cornea 4062.

In the embodiment illustrated in FIG. 4A, the rigid contact lens element 402 also comprises an outer surface 404 adapted for contacting the eyelid 408 and tear film thereon, and its inner surface 403 is also preferably adapted for contacting at least the surface 4061 of the eye 406, preferably also the tear film thereon (the tear films are again not illustrated for simplicity), and in particular such that its peripheral area 409 rests on the sclera 4063 of the eye 406, providing also the intermediate space 405.

However, in the variant illustrated in FIG. 4A, the passive sensing means 401 is chosen with a resonance frequency around 30 MHz, such that $\varepsilon_r$ (cornea)≈$\varepsilon_r$ (tear film)>>$\varepsilon_r$ (air)≈$\varepsilon_r$ (lens material). Thus, in order to efficiently detect any deformation of the surface 4061, or in other words in order to provide for at least one sensing capacitor between the coplanar elements of the passive sensing means 401 and opposite areas of the surface 4061, it is necessary to avoid that the space 405 is filled with tear film. Thus, in the variant illustrated in FIG. 4A, the physiological parameter monitoring system 400 comprises a multilayered contact lens 420, comprising the rigid lens 402, as well as a soft layer 410, which can be for instance a soft contact lens, joined at the edges towards the peripheral area 409, enclosing the intermediate space 405. The soft lens 410 also comprises an inner surface 411 adapted for contacting the surface 4061 and tear film thereon, as well as an outer surface 412 opposite the inner surface 411. In order to improve the contact with the surface 4061 of the eye 406, in particular of the cornea 4062, the multilayered lens 420, and in particular the soft lens 410, can avoid contact around the limbus area 4064 of the eye 406, while the peripheral area 409 rests on the sclera 4063.

Thus, in the variant illustrated in FIG. 4A, the tear film on the surface 4061 of the eye 406 can be considered to form part of the cornea 4062, while the soft lens 410 can be considered as one with the intermediate space 405, which can be filled with air or any other compressible and biocompatible material with a comparable low relative permittivity. In this embodiment, the distance d from the passive sensing means 401 to the inner surface 411 of the soft lens 410, in other words to the interface between the soft lens 410 and the tear film on the corneal area 4062, is smaller than the distance D between the passive sensing means 401 and the outer surface 404 of the rigid contact lens 402, such that any parasitic capacitance between the passive sensing means 401 and the eyelid 408 will be either negligible or non-existent compared to the parasitic capacitances of the sensing capacitors formed by the passive sensing means 401 and respective opposite areas of the surface 4061.

FIG. 4B illustrates a variant of a physiological parameter monitoring system 400', which is essentially the same as the physiological parameter monitoring system 400 illustrated in FIG. 4A, with the exception that the sensing means 401 is accommodated in a recess 4031 provided in the inner surface 403 of the rigid part 402 of the multilayered lens 420. This variant is then more advantageous than the previous variant in terms of attachment stability of the passive sensing means 401 within the multilayered lens 420.

FIGS. 5 to 8 illustrate further embodiments of passive sensing means according to the present invention. As mentioned above, these variants can all be used as alternatives to the variant illustrated in FIG. 1, and in particular these variants can all be used in the physiological monitoring systems 200, 300, 400, 400' described in the embodiments referring to FIGS. 2 to 4. The reader is therefore referred back to the description above regarding any features of the passive sensors 500, 600, 700, 800 of the embodiments illustrated in FIGS. 5 to 8 that are analog to those of the passive sensor 100 illustrated in FIG. 1, as well as regarding the use in combination with any of the physiological parameter monitoring systems 200, 300, 400, 400' of the embodiments illustrated in FIGS. 2 to 4.

In the embodiment illustrated in FIG. 5, like the passive sensor 100 of the embodiment illustrated in FIG. 1, the passive sensor 500 is a resonant circuit comprising an inductive element, here inductor 501, and at least one capacitive element, here the plurality of capacitors 521, 522, 523, 524, 525 and 526, which are all coplanar in one layer prior to any deformation of the passive sensor 500 for its incorporation in a contact lens of a physiological parameter monitoring system. The conductive, preferably metallic, elements 501, 521, 522, 523, 524, 525, 526 can also be provided on a layer of a carrier substrate, with or without protective coating layers thereon, which is again not illustrated for clarity purposes and can also be partially removed as described above.

Following a preferred variant, the inductor 501 of the embodiment illustrated in FIG. 5 is substantially of the same type and has the same properties and advantages as the inductor 101 of the embodiment illustrated in FIG. 1. In particular, it can also comprise concave arc-shaped segments 5011, 5012, 5013 with respect to—but not centered on—a substantially central reference point 510 of the passive sensor 500, as well as convex arc-shaped segments 5021, 5022, 5023 joining the concave segments 5011, 5012, 5013 to one another. Similarly, the inductor 501 can further comprise straight inductor segments 5031, 5032, 5033, 5034, 5035, 5036 and rounded junctions 5041, 5042, 5043, 5044, 5045, 5046 between the straight segments 5031, 5032, 5033, 5034, 5035, 5036 and the concave segments 5011, 5012, 5013.

Also like the inductor 101 illustrated in FIG. 1, the inductor 501 of the embodiment illustrated in FIG. 5 can also be a flat spiral inductor with a first terminal 5051 on the inner circumference of the concave arc-shaped segment 5012 and a second terminal 5052 on the outer circumference thereof, as well as a small deflected area 506. The inductor 501 can also comprise successive spires, for instance about 5 to 20 spires, preferably 8 to 15 spires, more preferably 10 to 13 spires, and its width can also preferably be kept below about 2.0 mm, for instance at about 1.5 mm or even below. In contrast with the inductor 101 of the embodiment illustrated in FIG. 1, the inductor 501 of the embodiment illustrated in FIG. 5 comprises 13 spires, which can have a width of about 50 μm and be spaced apart by also about 50 μm.

As further illustrated in FIG. 5, the capacitors 521, 522, 523, 524, 525, 526 can also be coplanar capacitors and are in fact very similar to the capacitors 121, 122, 123, 124, 125, 126 of the embodiment illustrated in FIG. 1. Thus, the pairs of electrodes 5211 and 5212, 5221 and 5222, 5231 and 5232, 5241 and 5242, 5251 and 5252, and 5261 and 5262 can also be coplanar to one another and form interdigitated E-shapes. Here also, the capacitors 521, 522, 523, 524, 525, 526 are provided in a coplanar manner —prior to bending the sensor 500—with the inductor 501, with the corresponding advantages described above. Similarly, capacitors 521 and 522 are provided in segment 5011, while capacitors 523 and 524 are provided in segment 5012, and capacitors 525 and 526 are provided in segment 5013. Furthermore, the first electrodes 5211 and 5221, 5231 and 5241, and 5251 and 5261, can also be electrically connected to the innermost spire of the inductor 501 and be provided as extensions of or be integral with the innermost spire, while the second electrodes 5212 and 5222, 5232 and 5242, and 5252 and 5262, can be connected to the outermost spire by means of respective electrically conductive vias 5213, 5223, 5233, 5243, 5253, 5263, as described above.

In the embodiment illustrated in FIG. 5, and in contrast with the embodiment illustrated in FIG. 1, while the capacitors 521, 522, 523, 524, 525, 526 can also be larger towards the innermost spire of the inductor 501 than towards the central point 510, they broaden again towards the central area 530—which can be free of material—surrounding the central point 510, such that their extremities are partially arc-shaped, in particular following the geometry of the convex arc-shaped segments 5021, 5022, 5023, with the advantage over the embodiment of FIG. 1 that more underlying surface of the eye, in particular over the cornea, can be covered once the passive sensor 500 is integrated in a physiological parameter monitoring system, for instance in any of the physiological parameter monitoring systems 200, 300, 400, 400'. In particular, as the innermost extremities of all electrodes 5211, 5212, 5221, 5222, 5231, 5232, 5241, 5242, 5251, 5252, 5261, 5262 become broader, the back of the E-shaped first electrodes 5211, 5221, 5231, 5241, 5251, 5261 follows partially the arc-shaped geometry of the nearby respective convex segment 5021, 5022, 5023.

In the embodiment illustrated in FIG. 6, the passive sensor 600 is also a resonant circuit comprising an inductive element, here the same inductor 501 as in the embodiment illustrated in FIG. 5, and at least one capacitive element, here the three capacitors 621, 622, 623, which are all coplanar in one layer prior to any deformation of the passive sensor 600 for its incorporation in a contact lens of a physiological parameter monitoring system. The reader is referred to the description above in particular regarding specifically the inductor 501, as well as other features in common with the passive sensors 100, 500 of the previous embodiments.

In contrast with FIGS. 1 and 5, only one capacitor 621, 622, 623 is provided at the inner circumference of each concave arc-shaped segment 5011, 5012, 5013, respectively. Like in the embodiments illustrated in FIGS. 1 and 5, each capacitor 621, 622, 623 of the embodiment illustrated in FIG. 6 is also coplanar, but the first and second electrodes in each pair of electrodes 6211 and 6212, 6221 and 6222, 6231 and 6232, are not interdigitated with each other. However, as illustrated in FIG. 6, each individual electrode 6211, 6212, 6221, 6222, 6231, 6232 is itself an interdigitated electrode. As further illustrated, each individual electrode 6211, 6212, 6221, 6222, 6231, 6232 of the passive sensor 600 can cover roughly at least as much surface as a full interdigitated capacitor 521, 522, 523, 524, 525, 526 of the passive sensor 500 of the embodiment illustrated in FIG. 5 or, in variants, as a full interdigitated capacitor 121, 122, 123, 124, 125, 126 of the passive sensor 100 of the embodiment referring to FIG. 1. In terms of shape, compared in particular to the embodiment illustrated in FIG. 5, in the embodiment illustrated in FIG. 6, each electrode 6211, 6212, 6221, 6222, 6231, 6232 roughly corresponds to having the two interdigitated E-shaped electrodes 5211 and 5212, 5221 and 5222, 5231 and 5232, 5241 and 5242, 5251 and 5252, and 5261 and 5262 of each capacitor 521, 522, 523, 524, 525, 526 joined at their largest extremity —towards the innermost spire of the inductor 501—thereby forming a single integral interdigitated electrode. An advantage of shaping the individual electrodes 6211, 6212, 6221, 6222, 6231, 6232 in this way is that it facilitates the molding or shaping of the passive sensor 600 for its attachment to a contact lens. As illustrated in FIG. 6, in an analog manner to the embodiment illustrated in FIG. 5, the back of the electrodes 6211, 6212, 6221, 6222, 6231, 6232 facing the convex arc-shaped segments 5021, 5022, 5023 of the inductor 501 can also follow the arc-shaped geometry of the convex arc-shaped segments 5021, 5022, 5023 and broaden towards the central area 530, with the same advantage over the embodiment of FIG. 1 that more underlying surface of the eye, in particular over the cornea, can be covered once the passive sensor 600 is integrated in a physiological parameter monitoring system, for instance in any of the physiological parameter monitoring systems 200, 300, 400, 400'.

Furthermore, like in the previous embodiments, the first electrodes 6211, 6221, 6231 of the passive sensor 600 can be electrically connected to the innermost spire of the inductor 501 and can be provided as integral extensions thereof, while the second electrodes 6212, 6222, 6232 can be connected to the outermost spire by means of respective electrically conductive vias 6213, 6223, 6233, which can also comprise a respective conductive bridge. FIG. 6 also illustrates that the vias 6213, 6223, 6233 can cross the carrier substrate and even the second electrodes 6212, 6222, 6232. An advantage of this configuration in the embodiment illustrated in FIG. 6 is, in comparison to the embodiments illustrated in FIGS. 1 and 5, that the number of electrically connecting vias is halved, thereby reducing the amount of areas where material crosses the carrier substrate, while keeping at least the same amount of surface covered by coplanar capacitors.

In the embodiment illustrated in FIG. 7, like the passive sensors 100, 500, 600 of the embodiments illustrated in FIGS. 1, 5 and 6, the passive sensor 700 is also a resonant circuit comprising an inductive element, here inductor 701, and at least one capacitive element, here the plurality of capacitors 721, 722, 723, 724, 725, 726, 727, 728 which are all coplanar in one layer prior to any deformation of the passive sensor 700 for its incorporation in a contact lens of a physiological parameter monitoring system. These conductive, preferably metallic, elements 701, 721, 722, 723, 724, 725, 726, 727, 728 can also be provided on a layer of a carrier substrate, with or without protective coating layers thereon, which is again not illustrated for clarity purposes and can also be partially removed as described above.

Following a preferred variant, in alternative to the embodiments illustrated in FIGS. 1, 5 and 6, the inductor 701 of the embodiment illustrated in FIG. 7 is a flat circular ring-shaped inductor spiraling from a first terminal 7051 on its innermost circumference towards a second terminal 7052 on its outermost circumference. While the inductors 101 and 501 of the previous embodiments and their variants can be more advantageous in terms of facilitating the deformation of the passive sensors 100, 500, 600 in view of their attachment to the concave cap-shape of a contact lens, the inductor 701 of the passive sensor 700 of the embodiment illustrated in FIG. 7 is in turn more advantageous in terms of the amplitude of the signal at the antenna of a complementary portable device generating the external magnetic field. Like in the previous embodiments, the inductor 701 can also comprise successive spires, for instance about 5 to 20 spires, preferably 8 to 15 spires, more preferably 10 to 13 spires, and its width can also preferably be kept below about 2.0 mm, for instance at about 1.5 mm or even below. Like the inductor 501 of the embodiment illustrated in FIGS. 5 and 6, the inductor 701 of the embodiment illustrated in FIG. 7 can thus comprises 13 spires, which can have a width of about 50 μm and be spaced apart by also about 50 μm.

In order to provide sufficient surface coverage in view of using the passive sensor 700 for detecting deformations of the surface of an eye while still providing for sufficient flexibility for an attachment to a contact lens, in the embodiment illustrated in FIG. 7, a plurality of capacitors are provided, here the eight coplanar interdigitated capacitors 721, 722, 723, 724, 725, 726, 727, 728. In view of the description above, the skilled person will understand that this number should not be seen as restrictive, and that more or less capacitors can be used depending on the desired configuration and sensitivity of the passive sensing means.

As further illustrated in FIG. 7, the capacitors 721, 722, 723, 724, 725, 726, 727, 728 are of the same type as the capacitors 121, 122, 123, 124, 125, 126 of the embodiment illustrated in FIG. 1. Thus, the pairs of electrodes 7211 and 7212, 7221 and 7222, 7231 and 7232, 7241 and 7242, 7251 and 7252, 7261 and 7262, 7271 and 7272, and 7281 and 7282 can also be coplanar to one another, forming interdigitated E-shapes. Furthermore, the capacitors 721, 722, 723, 724, 725, 726, 727, 728 can also be larger towards the innermost spire of the inductor 701 than towards the central area 730, for instance such that the overall shape of each capacitor 721, 722, 723, 724, 725, 726, 727, 728 is essentially trapezoidal, with the larger base facing outwards from the central area 730 and the smaller base facing towards said central area 730, with the same advantages as described above for instance for the embodiment illustrated in FIG. 1.

Furthermore, as described also for the embodiments illustrated in FIGS. 1 and 5, in the passive sensor 700 of the embodiment illustrated in FIG. 7, the first electrodes 7211, 7221, 7231, 7241, 7251, 7261, 7271, 7281 can also be electrically connected to the innermost spire of the inductor 701 and be provided as extensions of or be integral with the innermost spire, while the second electrodes 7212, 7222, 7232, 7242, 7252, 7262, 7272, 7282 can be connected to the outermost spire by means of respective electrically conductive vias 7213, 7223, 7233, 7243, 7253, 7263, 7273, 7283 as also described above for the previous embodiments.

In the embodiment illustrated in FIG. 8, the passive sensor 800 is also a resonant circuit comprising an inductive element, here the same inductor 701 as in the embodiment illustrated in FIG. 7, and at least one capacitive element, here the four capacitors 821, 822, 823, 824, which are all coplanar in one layer prior to any deformation of the passive sensor 800 for its incorporation in a contact lens of a physiological parameter monitoring system. The reader is referred to the description above in particular regarding specifically the inductor 701, as well as other features in common with the passive sensors 100, 500, 600, 700 of the previous embodiments.

In contrast with the embodiment illustrated in FIG. 7, but similarly to the embodiment illustrated in FIG. 6, in the passive sensor 800, the first and second electrodes in each pair of electrodes 8211 and 8212, 8221 and 8222, 8231 and 8232, 8241 and 8242 of the capacitors 821, 822, 823, 824 are not interdigitated with each other. However, as illustrated in FIG. 8, each individual electrode 8211, 8212, 8221, 8222, 8231, 8232, 8241, 8242 can be in the shape of a trident pointing towards the central area 730, forming also a trapezoidal shape as described above, wherein the capacitors 821, 822, 823, 824 are also larger towards the innermost spire of the inductor 701 than towards the central area 730, with again the same advantages as described above for instance for the embodiment illustrated in FIG. 1. As further illustrated in FIG. 8, each individual electrode 8211, 8212, 8221, 8222, 8231, 8232, 8241, 8242 of the passive sensor 800 can cover roughly at least as much surface as a full interdigitated capacitor 721, 722, 723, 724, 725, 726, 727, 728 of the embodiment illustrated in FIG. 7.

Furthermore, like in the previous embodiments, the first electrodes 8211, 8221, 8231, 8241 of the passive sensor 800 can be electrically connected to the innermost spire of the inductor 701 and can be provided as integral extensions thereof, while the second electrodes 8212, 8222, 8232, 8242 can be connected to the outermost spire by means of respective electrically conductive vias 8213, 8223, 8233, 8243 and respectively associated conductive bridges. Like in the embodiment illustrated in FIG. 6, an advantage of this configuration in the embodiment illustrated in FIG. 8 is, in comparison to the embodiment illustrated in FIG. 7, that the number of electrically connecting vias is halved, thereby reducing the amount of areas where material crosses the carrier substrate, while keeping at least the same amount of surface covered by coplanar capacitors.

As mentioned above, any of the passive sensors 100, 500, 600, 700, 800 of the embodiments illustrated in FIG. 1 or 5 to 8, or any of their variants, can be used in the physiological parameter monitoring systems 200, 300, 400, 400' of the embodiments illustrated in FIGS. 2 to 4B or variants thereof. Indeed, when the passive sensing means 100, 500, 600, 700, 800 respond to an external magnetic field generated by a complementary portable device, the configuration of the inductor and/or of the capacitors in each of the passive sensors 100, 500, 600, 700, 800 allows the electric field lines generated therein to protrude out of the plane of the passive sensor 100, 500, 600, 700, 800. Thus, when used in any of the physiological parameter monitoring systems 200, 300, 400, 400', parasitic capacitances will exist with the underlying eye tissue and/or tear film thereon, which will form sensing capacitors, wherein the spires of the inductor and/or the physical capacitors of the passive sensors 100, 500, 600, 700, 800 are first electrodes of said sensing capacitors, and the eye tissue and/or the tear film are the second electrodes thereof.

The skilled person will find it obvious that the embodiments described above can be combined in order to provide further embodiments of the various aspects of the present invention. In particular, the variants of a passive sensing means can all be used in either variant of the physiological parameter monitoring systems.

The skilled person will also appreciate that the present invention provides an improvement in the field of passive sensing devices for monitoring variations of a physiological parameter, in particular for monitoring variations of the intraocular pressure. The passive sensing device and the physiological parameter monitoring device according to preferred variants of aspects of the present invention can be used advantageously for patients suffering from glaucoma and related eye diseases. Compared to solutions known in the art, the aspects of the present invention provide a sensing device with improved sensitivity and improved flexibility for integration or attachment in a contact lens. The invention also provides a new physiological parameter monitoring system for detecting variations of parameters that can be correlated to variations of the physiological parameter.

The invention claimed is:

1. A physiological parameter monitoring system for detecting variations of intraocular pressure, comprising:
   a first contact lens element, having an inner surface and an outer surface opposite the inner surface, with a peripheral area adapted for contacting the sclera such that an intermediate space is provided between the inner surface and an eye surface when the peripheral area contacts the sclera;

a passive sensing means forming a resonant circuit having a resonance frequency that varies as a function of intraocular pressure and comprising:
an inductor and at least one capacitor,
wherein the inductor and the at least one capacitor are coplanar in only one layer;
characterized in that said inductor and at least one capacitor are arranged such that they form first electrodes of at least one sensing capacitor,
wherein the passive sensing means is configured such that at least one of an underlying surface and a tear film of an eye wearing the contact lens act as at least one corresponding second electrode of the at least one sensing capacitor when the contact lens is positioned in contact with the eye.

2. The physiological parameter monitoring system according to claim 1, wherein the inductor is a flat inductor comprising a plurality of concave arc-shaped segments with respect to a substantially central point of the passive sensing means, and wherein for at least one of the plurality of concave arc-shaped segments, the radius of curvature of the at least one segment at a point thereof is greater than the distance between the point and the substantially central point.

3. The physiological parameter monitoring system according to claim 2, wherein the inductor further comprises convex arc-shaped segments arranged between the concave arc-shaped segments.

4. The physiological parameter monitoring system according to claim 3, wherein the inductor further comprises straight segments joining the convex arc-shaped segments to the concave arc-shaped segments, and wherein the junctions between said straight segments and the concave arc-shaped segments are rounded.

5. The physiological parameter monitoring system according to claim 3, wherein the at least one capacitor is larger towards the inner circumference of the inductor than towards the central area.

6. The physiological parameter monitoring system according to claim 5, wherein the at least one capacitor is partially arc-shaped following the convex arc-shaped segments at its extremity towards the central area.

7. The physiological parameter monitoring system according to claim 2, wherein said at least one capacitor is provided at an inner circumference of the inductor towards a central area of said passive sensing means.

8. The physiological parameter monitoring system according to claim 7, wherein, for at least one of the plurality of inductor concave arc-shaped segments, at least one capacitor is provided at an inner circumference thereof towards a central area of the passive sensing means.

9. The physiological parameter monitoring system according to claim 7, wherein, for all of the plurality of inductor concave arc-shaped segments, at least one capacitor is provided at an inner circumference thereof towards a central area of the passive sensing means.

10. The physiological parameter monitoring system according to claim 1, wherein the inductor is circular ring-shaped.

11. The physiological parameter monitoring system according to claim 1, wherein the inductor is a spiral inductor.

12. The physiological parameter monitoring system according to claim 11, wherein the width of one or more of a plurality of spires of the spiral inductor and/or the distance between at least two of the plurality of spires is in a range from about 30 µm to about 100 µm such that the total width of the inductor is about 2 mm or less.

13. The physiological parameter monitoring system according to claim 1, wherein said at least one capacitor is a coplanar capacitor.

14. The physiological parameter monitoring system according to claim 1, wherein the at least one capacitor comprises a first electrode and a second electrode, and wherein the first electrode is electrically connected to an inner circumference of the inductor and the second electrode is electrically connected by means of an electrically conductive via, to an outer circumference of the inductor.

15. The physiological parameter monitoring system according to claim 14, wherein at least one of the at least one capacitor, or the first electrode, and the second electrode is interdigitated.

16. The physiological parameter monitoring system according to claim 1, wherein the passive sensing means is provided in a recess of the inner surface of the first contact lens element.

17. The physiological parameter monitoring system according to claim 16, further comprising a second contact lens element comprising a hydrophilic flexible polymer material, having an inner surface and an outer surface opposite the inner surface, wherein at least the inner surface of the second contact lens element is adapted for contacting an ocular tissue, and wherein the first lens element and the second lens element are attached to one another at a peripheral attachment area, thereby enclosing an intermediate space.

18. The physiological parameter monitoring system according to claim 16, further comprising a second contact lens element comprising a flexible material having an inner surface and an outer surface opposite the inner surface, wherein at least the inner surface of the second contact lens element is adapted for contacting an ocular tissue, and wherein the first lens element and the second lens element are attached to one another at a peripheral attachment area, thereby enclosing an intermediate space.

19. The physiological parameter monitoring system according to claim 1, wherein the inductor is a spiral inductor comprising 5 to 20 spires.

20. The physiological parameter monitoring system according to claim 1, wherein the first contact lens element comprises a rigid polymer material.

* * * * *